United States Patent [19]

Heimke et al.

[11] Patent Number: 5,405,385
[45] Date of Patent: Apr. 11, 1995

[54] INTRAOCULAR LENS WITH INTEGRATED MEANS OF FIXATION

[75] Inventors: Gunther Heimke, Clemson; Andreas F. Von Recum, Six Mile, both of S.C.; Frank M. Polack, Gainesville, Fla.

[73] Assignee: Clemson University, Clemson, S.C.

[21] Appl. No.: 20,226

[22] Filed: Feb. 16, 1993

Related U.S. Application Data

[63] Continuation of Ser. No. 861,936, Apr. 2, 1992, abandoned.

[51] Int. Cl.⁶ .............................................. A61F 2/16
[52] U.S. Cl. ........................................................ 623/6
[58] Field of Search ............................................. 623/6

[56] References Cited

U.S. PATENT DOCUMENTS

| | | |
|---|---|---|
| 4,449,257 | 5/1984 | Koeniger ................... 623/6 |
| 4,704,123 | 11/1987 | Smith ....................... 623/6 |
| 4,808,181 | 2/1989 | Kelman . | |
| 4,846,832 | 7/1989 | Wichterle ................. 623/6 |
| 4,865,601 | 9/1989 | Caldwell ................... 623/5 |
| 4,932,968 | 6/1990 | Caldwell ................... 623/6 |
| 5,011,494 | 4/1991 | von Recum et al. ....... 623/11 |

OTHER PUBLICATIONS

Apple et al, "Intraocular Lenses: Evolution, Designs, Complications, and Pathology", Chapters 1-2, pp. 1-41.
Green et al, "Fibroblast Response to Microtextured Silicone Surfaces: Texture Orientation into or out of the Surface", Journal of Biomedical Materials Research, vol. 28, pp. 647-653 (1994).
Blomstedt et al, "After-Cataract in the Rabbit Eye Following Extracapsular Cataract Extraction—A Wound Heal Reaction", Ophthalmologica, vol. 65, Suppl. 182, pp. 93-99 (1987).
McDonald et al, "After-Cataract of the Rabbit: Autoradiography and Electron Microscopy", Annals of Ophthalmology, pp. 37-50 (Jan. 1974).
Ishibashi et al, "Fine Structure on Top of Intraocular Lens Surface: A Transmission Electron Microscopic Study", Cells and Materials, vol. 1, No. 4, pp. 301-306 (1991).
Jacob et al, "Cytological Factors Relating to Posterior Capsule Opacification Following Cataract Surgery", British Journal of Ophthalmology, vol. 71, pp. 659-663 (1987).
C. E. Campbell and A. F. von Recum, "Microtopography and Soft Tissue Response", J. Investig. Surg. vol. 2 pp. 51-74 (1989).

*Primary Examiner*—Randy C. Shay
*Attorney, Agent, or Firm*—Dority & Manning

[57] ABSTRACT

An intraocular lens has an optic body with at least a posterior surface defining a roughness portion disposed close to the periphery of the optic body wherein the roughness portion further defines an attachment configuration specified by parameters falling within certain specific ranges determined statistically using a profilometer. The parameters measure on the order of micrometers. The attachment configuration holds the lens in place without the use of spiral shaped fibrous arms.

15 Claims, 7 Drawing Sheets

INTRAOCULAR LENS WITH INTEGRATED MEANS OF FIXATION

This is a continuation of application Ser. No. 07/861,936, filed Apr. 2, 1992, which was abandoned upon the filling hereof.

BACKGROUND OF THE INVENTION

The present invention relates to intraocular lenses and more particularly to such lenses having some means for fixation in the eye.

During the nineteen seventies, early attempts were made to use intraocular lenses to replace the human eye lenses that were removed during cataract surgery. The success rates for these intraocular lens replacements have steadily increased during the nineteen eighties. During about the last five years, intraocular lens implants have become a standard treatment following cataract operations. Now, more than half of all removed lenses are replaced by such implants. In the U.S. alone, about 2,000,000 cataract operations are performed annually, of which now about 90% are provided with intraocular lenses.

Recently, soft and foldable lenses made of silicone have found increasing attention. Because they can be folded for purposes of insertion into the eye, they require a smaller incision than required by a conventional lens, thus considerably reducing the operational trauma. The diameter of one of these silicone lenses is about two thirds of the diameter of the natural lens itself. To facilitate its correct positioning upon its unfolding and final stabilization in the lens cavity of the eye, the silicone lens carries two spiral shaped, relatively stiff fibers on opposite sides of the lens. These fibers are intended to rest along the outside periphery of the lens cavity.

In a relatively high number of cases, however, one of these spiral fibers may not find its intended position but rather comes to rest in the anterior chamber from which it cannot be removed in all cases. Also, the forces exerted by these fibers onto the periphery of the lens capsule can stimulate some granulation tissue formation. Such granulation tissue is undesirable as it leads to displacement of the lens and opacification of the posterior capsule of the eye.

The lens described in U.S. Pat. No. 4,449,257 to Koeniger is formed of a soft HEMA plastic that is cut and shaped when dry to a shape that will expand and soften with the uptake of aqueous humor in the eye. In this way, the lens will expand to fill the posterior capsule of the eye's posterior chamber. The round lens has a plurality of concentric grooves 12 cut into marginal peripheral areas on both sides of the lens. Grooves 12 are disclosed to frictionally engage the eye capsule's inside walls, which are naturally rough. The grooves are intended to hold the lens firmly in place without any clips, loops, and/or staves and sutures.

The Smith patent (U.S. Pat. No. 4,704,123) describes a soft intraocular lens having an optic portion and two fenestrated haptics extending from opposite peripheral edges of the optic. Each fenestrated haptic includes a tissue contact portion remote from the optic, first and second beam portions extending from opposite ends of the tissue contact portion in a direction towards the optic and tapering so as to widen in a direction measured in the plane of the fenestration when proceeding from the tissue contact portion toward the optic. The beam portions of the haptic also widen in a direction measured generally parallel to the optic axis when proceeding from the tissue contact portion toward the optic. Each beam portion is connected to the optic by a support portion which widens in the plane of the fenestration as one proceeds from the beam portion toward the optic, but narrows in the direction of the optical axis when one proceeds from the beam portion toward the optic.

These intraocular lenses with their various mechanical means of securing the lens in the eye cavity cannot ensure against movement of the lens over time or against the formation of granulation tissue and eventual opacification of the posterior capsule of the eye.

OBJECTS AND SUMMARY OF THE INVENTION

It is a principal object of the present invention to provide an intraocular lens that has means for retaining the lens in the proper position without subsequent movement of the lens or causing formation of granulation tissue or opacification of the posterior capsule of the eye.

It is another principal object of the present invention to provide an intraocular lens that has means for becoming integrated with the eye tissue and thereby held in position and restrained from movement from the proper position within the eye without causing formation of granulation tissue or opacification of the posterior capsule of the eye.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an intraocular lens is configured with a diameter close to that of the natural lens. A roughness of the lens surface is defined on at least one side of the lens. Desirably, the roughness is confined at or close to the outside rim or circumference of the optic body of the lens. The surface area of the lens occupied by the roughness portion can take many shapes, including a band along the outside circumference. The roughness band desirably is concentric with the optic axis of the lens and has a radial breadth of from 0.5 to 1 millimeters. However, the dimensions of the surface features that constitute the roughness configuration, must stay within well defined limits. The desired configuration of the roughness portion is the so-called "attachment configuration" of the present invention.

The attachment configuration according to this invention consists of a particular kind of roughness which can be described in terms of certain parameters of the configuration, which can include gaps and protrusions, that define the surface. In accordance with the present invention, the surface roughness has the attachment configuration of the present invention provided that for a statistically significant sample of nonparallel unidirectional sampling paths taken within the roughness portion on the lens surface, each path having an orthogonal projection $M_P$ measuring at least one-tenth millimeter in length on a flat plane, each of the mean values of the parameters S, D, T and G, satisfy the range wherein: (1) the mean D value is larger than 0.5 micrometers, (2) each of the mean values of G and T is from 0.5 to 5 micrometers, and (3) the mean S value is from 1 to 10 micrometers. Desirably, the measurements of each of the parameters (S) protrusion spacing, (D) gap depth, (T) half-height protrusion thickness, and (G) half-height gap width, can be obtained using a surface profilometer. In a particularly desirable embodiment of the attachment configuration, the mean value of the half-height widths G of the gaps and half-height thicknesses T of the protrusions is from 1 to 4 micrometers, the mean value of the depths D of the gaps is at least 0.5 micrometers, and the mean value of the spacings S between the adjacent protrusions is in the range from 1 to 4 micrometers.

In one preferred embodiment, the attachment configuration includes concentric circular grooves of one to four micrometers depth and radial width and one to four micrometers radial distance between adjacent grooves.

Alternatively, in a second preferred embodiment, the lens of the present invention is smaller than the natural lens, but is provided with a haptic portion in the form of an annular disk-shaped ring surrounding the optic body of the lens. The outside rim of the disk-shaped ring has a roughness band provided with the attachment configuration.

A third preferred embodiment of the present invention is similar to the second embodiment described above, except that the disk-shaped ring can be perforated through the haptic portion between the roughness band and the outer periphery of the optic body portion of the lens.

In a fourth preferred embodiment of the present invention the plane of the disk-shaped ring is tilted relative to the plane of the optic body of the lens toward either the posterior surface or the anterior surface of the lens by up to about 30 degrees.

In yet another embodiment of the present invention, the attachment configuration is provided in the entire posterior surface of the optic body of the lens and/or the haptic portion, if any.

The accompanying drawings, which are incorporated in and constitute a part of this specification, illustrate several embodiments of the invention and, together with the description, serve to explain the principles of the invention.

BRIEF DESCRIPTION OF THE DRAWINGS

Each of FIGS. 9-12 is a graphical representation of the profilometer path 400 followed in the embodiment shown in FIG. 8 and is intended to illustrate schematically various important dimensions of the attachment configuration of this embodiment of the present invention.

DETAILED DESCRIPTION OF THE PREFERRED EMBODIMENTS

Reference now will be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations come within the scope of the appended claims and their equivalents. The same numbers are used in each of the Figs. to designate the same or equivalent features.

In studies of tissue reactions to implant surfaces carrying different kinds of surface roughness (gaps and protrusions) having mean dimensions in the size range of 0.4 to 10 $\mu$m, but with all other parameters being kept constant, the following phenomenon was observed. According to this phenomenon, for surface gaps and protrusions having mean dimensions in the size range between 1 to 4 $\mu$m, a thin, well adherent, stable and non-contracting connective tissue film was observed. Moreover, for surface gaps and protrusions having mean dimensions larger than this size range, macrophages and giant cells were found as well as the formation of a granulation tissue capsule. Furthermore, for surface gaps and protrusions having mean dimensions smaller than this size range, macrophages and giant cells were found. These observations turned out to be widely independent of the chemistry of the material forming the topography of the surface. See C. E. Campbell and A. F. von Recum, "Microtopography and Soft Tissue Response", *J. Investig. Surg.* vol. 2 pages 51-74 (1989). See also U.S. Pat. No. 5,011,494 to von Recum et al, the disclosure of which is hereby incorporated herein by this reference.

Figure 3:
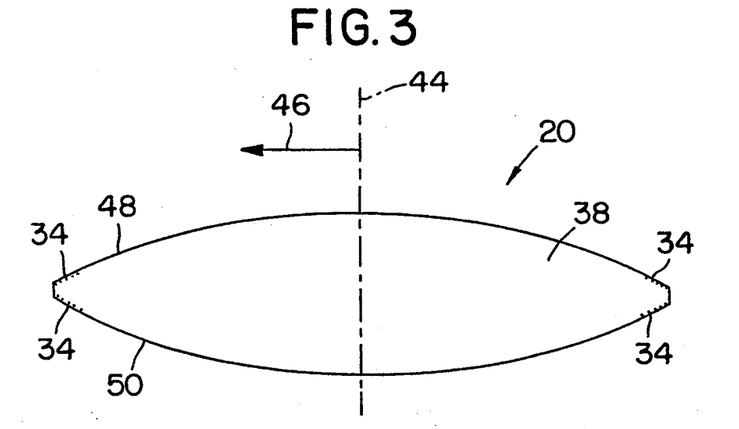
FIG. 3 is a side plan view of the embodiment of the present invention shown in FIGS. 1 and 2.

In accordance with the present invention, an intraocular lens can be formed of a diameter coming close to, if not equal to, that of the natural lens. A preferred embodiment of the intraocular lens of the present invention is shown in FIGS. 1 and 3 for example and is represented generally by the numeral 20.

Figure 5:
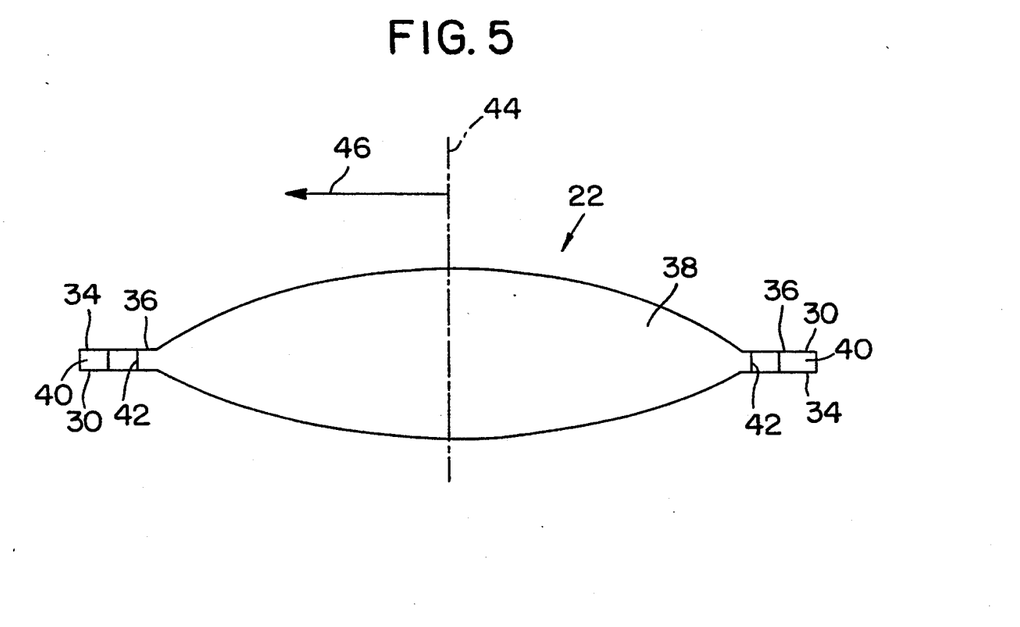
FIG. 5 is a cross-sectional view of the embodiment of FIG. 4 taken along a diameter of the embodiment of FIG. 4.
Figure 6:
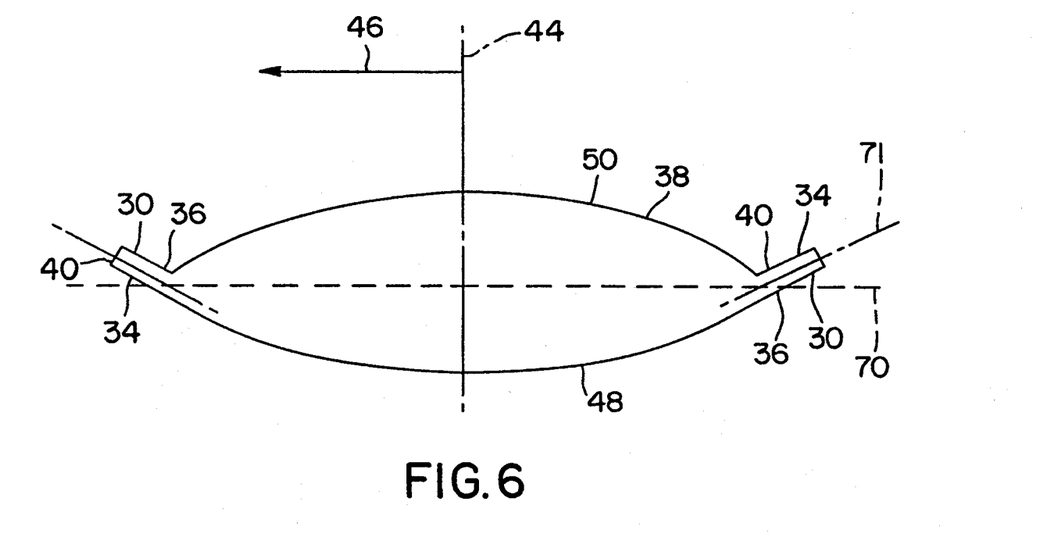
FIG. 6 is a cross-sectional view similar to FIG. 5, but of yet another embodiment of the present invention.

The optic body of the intraocular lens is the portion of the lens that refracts the light intended to be focused on the retina of the eye. As schematically shown in FIGS. 3, 5 and 6 for example, an optic body 38 has an optic axis 44, which is an imaginary line along which the light is not changing direction. Since the optic axis ordinarily is a centrally located axis, the optic axis is used herein as a convenient point of reference to locate other features of the lens of the present invention. For example, this optic axis constitutes the origin for lens measurements taken in the radial direction, which is designated by the line identified by the numeral 46 in FIGS. 3, 5 and 6.

Figure 1:
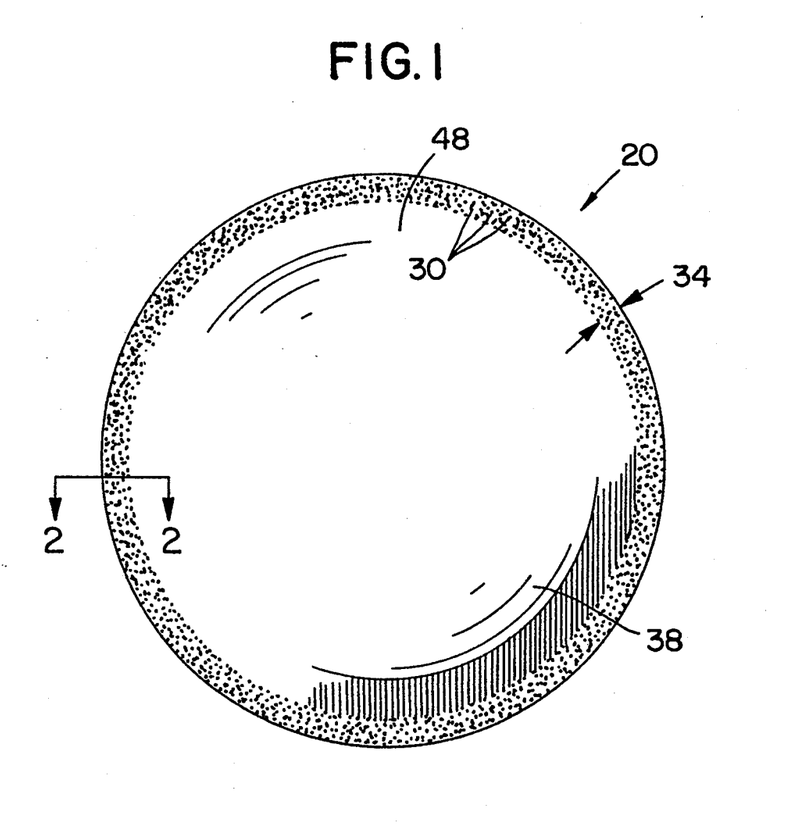
FIG. 1 is a top plan view of a preferred embodiment of the present invention.
Figure 4:
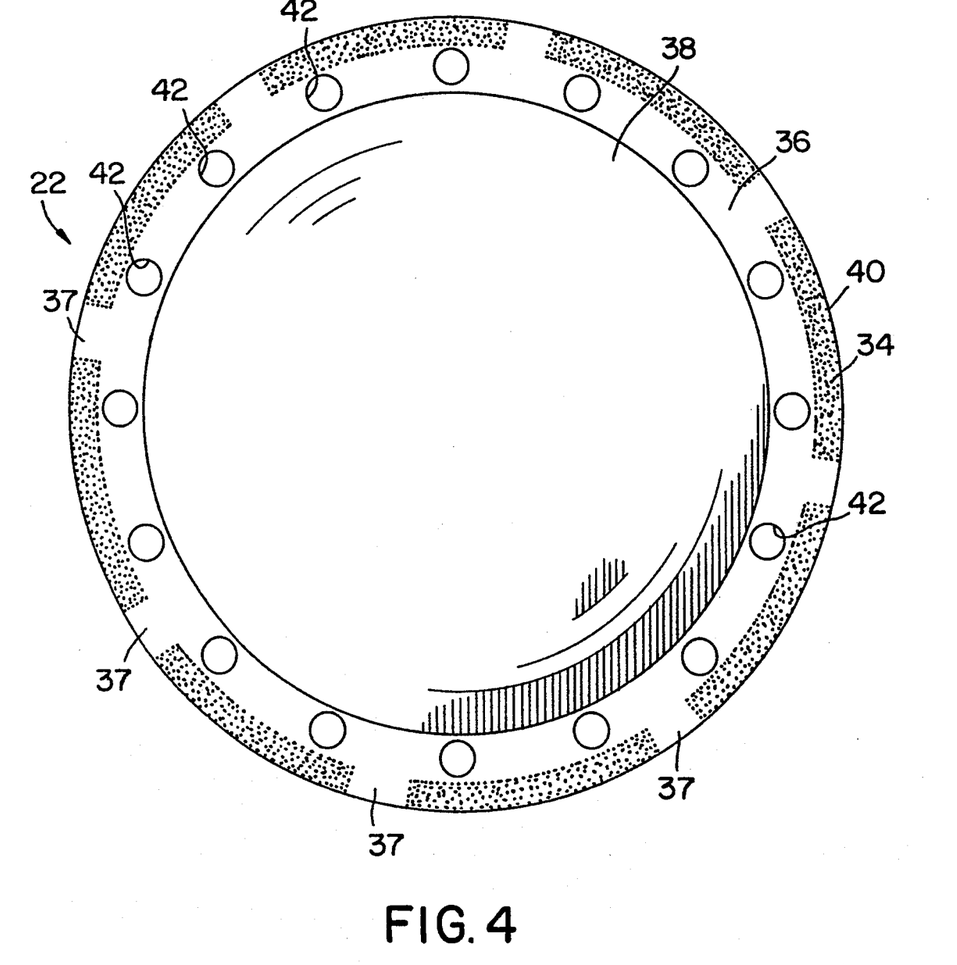
FIG. 4 is a top plan view of an alternative preferred embodiment of the present invention.

As shown in FIG. 1 from the perspective of a top plan view, lens 20 of the present invention includes a band area 34 indicated by the stippling near the edge of the lens. As shown in FIG. 1 for example, band portion 34 is formed as a generally circular band disposed about the optical axis (not shown). Desirably, the band portion's radial width, which is measured along the direction of the solid line drawn connecting the blunt ends of arrows A, A, is from 0.1 to 1 millimeter. In FIG. 4, the band area 34 is shown as a circular band in relation to the haptic disk-shaped ring 36. Again, the band portion's radial width is desirably from 0.1 to 1 millimeter.

The band portion or area or section 34 defines the portion of the lens surface forming the particular surface roughness 30 of the present invention (about which more is said later). As shown in FIG. 3 for example, band area 34 is desirably located near the periphery of the anterior surface 48 of the optic body 38 of lens 20 and near the periphery of the posterior surface 50, which is disposed opposite to anterior surface 48. In most embodiments, the surface roughness 30 is disposed as part of both the anterior surface and the posterior surface desirably near the periphery of optic body 38 and disposed farthest away from optic axis 44, which is in the center of optic body 38 and extending in a manner perpendicular to the plane of the drawing of FIG. 1.

Moreover, while the lens of the present invention is formed without the spiral shaped fibrous arms of some prior art lenses, the surface roughness 30 of the lens of the present invention is defined with a so-called "attachment configuration" in the form of a particular kind of roughness with well defined dimensions. As shown in FIGS. 1 and 3 for example, portions of the lens surfaces can include a concentric band 34 within which a surface roughness 30 with an attachment configuration is provided. The attachment configuration includes gaps having a mean value of more than 0.5 μm for the depth of the gap and a mean value of between 0.5 to 5 μm for the so-called half-height width of the gap. The attachment configuration includes protrusions having a mean value of between 0.5 and 5 μm for the so-called half-height thickness of the protrusions and a mean value of 1 to 10 μm for the so-called peak-to-peak spacings between adjacent protrusions.

In accordance with the present invention, the surface roughness has the attachment configuration of the present invention provided that for a statistically significant sample (at least 30 different noncoincident paths) of nonparallel unidirectional profilometer sampling paths, each path having an orthogonal projection $M_p$ measuring at least one-tenth millimeter in length on a flat plane, each of the mean values of the parameters S, D, T and G as shown in FIGS. 9-12 for example, satisfy the range wherein: (1) the mean D value is larger than 0.5 micrometers, (2) each of the mean values of G and T is from 0.5 to 5 micrometers, and (3) the mean S value is from 1 to 10 micrometers. In a particularly desirable embodiment of the attachment configuration, the mean value of the half-height widths G of the gaps and half-height thicknesses T of the protrusions is from 1 to 4 micrometers, the mean value of the depths D of the gaps is at least 0.5 micrometers, and the mean value of the spacings S between the adjacent protrusions is in the range from 1 to 4 micrometers.

A statistically significant sample would include measurements from at least 30 different noncoincident and nonparallel profilometer paths within band 34 formed in the surface of the lens. Thus, as long as after 30 different straight line projections $M_p$ of 30 profilometer paths on the surface within the band 34, no two of the 30 paths being coincident or parallel to each other, wherein the length of each of the projections $M_p$ measures at least one-tenth of a millimeter, the mean values of each of the parameters S, D, T and G fall within the designated ranges, then this surface has a roughness with the attachment configuration within the scope of the present invention. In other words, such a surface would have the particular kind of roughness specified according to the present invention.

Desirably, the measurements of each of the parameters S, D, T and G can be obtained using a surface profilometer. Brown & Sharpe of 27300 Haggerty Road, Farmington Hills, Mich. 48331 produces a line of SURFCOM surface profilometer instruments and the HANDY SURF E10 profilometer. Tencor Instruments of 2400 Charleston Road, Mountainview, Calif. 94043 produces the TENCOR P-1 LONG SCAN PROFILER surface profilometer. The profilometer maps the contour of a surface along the path over which the detecting probe of the profilometer moves. Typically, the profilometer permits the operator to select the cut-off length, which corresponds exactly to the sampling distance $M_P$. The measurements needed for the protrusion spacing (S), protrusion thickness (T), gap depth (D), and gap width (G) parameters can be obtained from the graphs generated by the profilometer. Then these graphs can be used to measure each of these parameters, and mean values can be calculated for the 30 sample path measurements.

Figure 8:
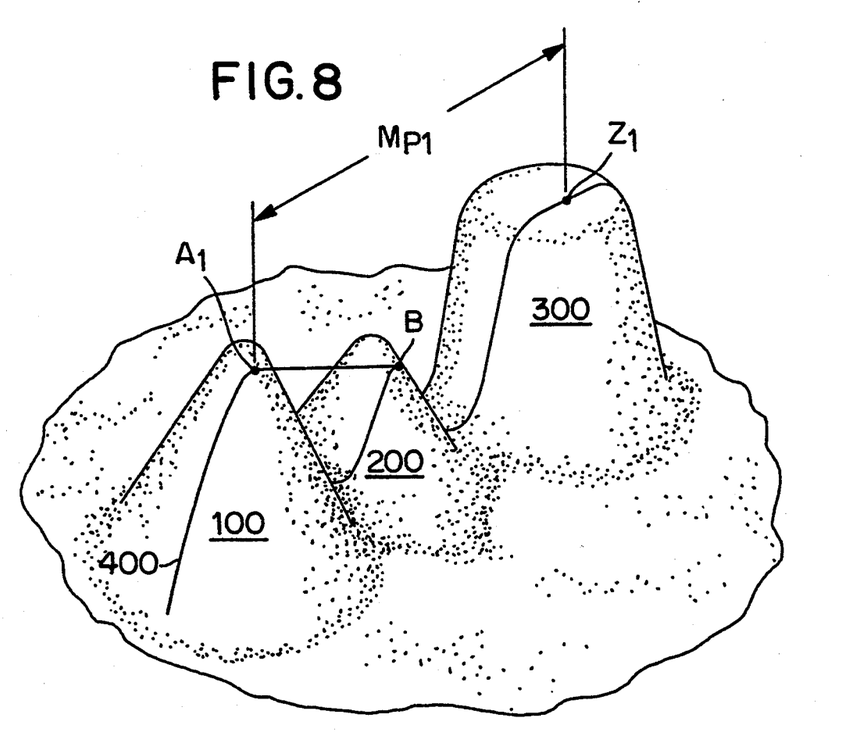
FIG. 8 is a schematic illustration of a partial, enlarged perspective view of an attachment configuration of the roughness band portion of an embodiment of the lens of the present invention.

The first parameter to be defined is the manner of measuring the sampling distance $M_P$, which as noted above is sometimes referred to in the profilometer art as the "cut-off length." Typically, a point will be selected as the starting point used in tracing the detection probe of the profilometer on the lens surface to be sampled within the attachment configuration. FIG. 8 schematically depicts a perspective view of an enlargement of a section within band 34 on the lens surface. However, in order to avoid obscuring certain features of the invention, all but three protrusions 100, 200, 300 have been omitted from the view shown in FIG. 8. As shown in FIG. 8 for example, a point "$A_1$" near the sharp peak of a protrusion 100 has been chosen arbitrarily as the starting point for tracing a path with the detection probe (not shown) of the profilometer. As shown in FIG. 8 for example, the projection $M_{P1}$ of the profilometer sampling path defined by a line $A_1$-$Z_1$ is the line $A_1$-$Z_1$ projected onto a flat plane. Thus, the line $A_1$-$Z_1$ represents the straight line path taken by the detection probe of the profilometer from point $A_1$, which is at the relative peak (the highest point in that immediate locality) of the protrusion 100, to point $Z_1$, which in FIG. 8 happens to be near the middle of a flat-topped protrusion 300. When the profilometer detection probe (not shown) is used to map the contour of the sampling path $A_1$-$Z_1$, the profilometer can generate in graphical format, a representation 400 such as shown in FIGS. 8-12 for example. Once this graphical format has been obtained, then the remaining parameters of interest, namely, S, D, T, and G, can be measured and recorded for this particular profilometer path $A_1-Z_1$.

Figure 9:
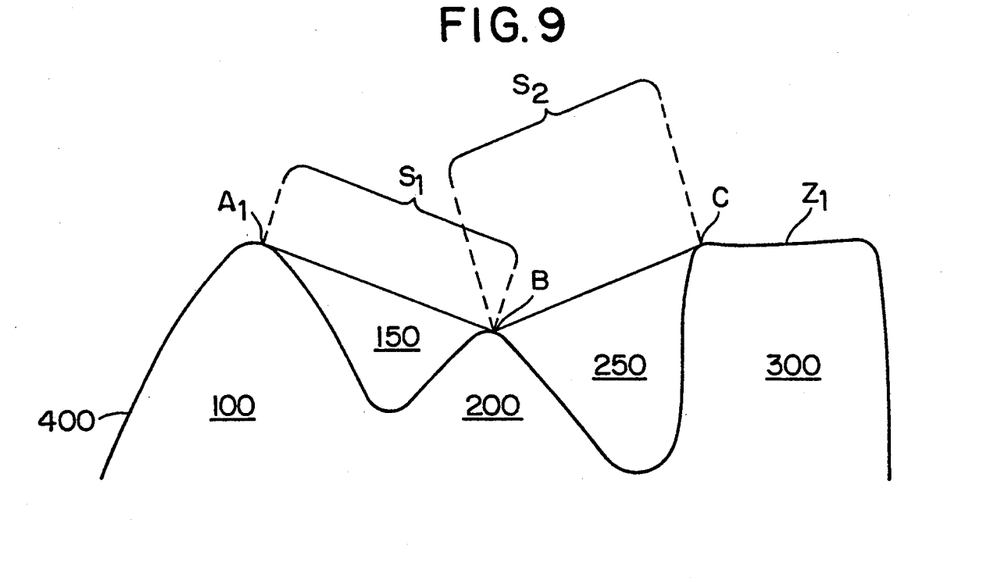

The first parameter is the so-called peak-to-peak spacing distance between adjacent protrusions 100, 200 in the sampling path and is represented by the letter S. This is only a precisely literal description when the direction of the path of the profilometer's sampling probe has been chosen so as to intersect the maximum points of two adjacent protrusions. Thus, another way of describing this protrusion spacing parameter S is the distance between the highest points on two adjacent protrusions in the path of the profilometer's sampling probe. As shown in FIG. 8 for example, the sampling probe path extends in a constant direction from point $A_1$ to point $Z_1$ and thus yields a straight line for the projection $M_{P1}$ of the path $A_1-Z_1$ onto a flat plane. Accordingly, as shown in FIG. 9 for example, at one end point $A_1$ of the straight line $A_1-B$ which defines the spacing distance $S_1$, the protrusion 100 has been intersected at its highest point in the imaginary vertically extending plane (not shown) containing both the projection $M_{P1}$ and the sampling path $A_1-Z_1$. Similarly, the opposite end point B of the straight line $A_1-B$ which defines the spacing distance $S_1$ is the localized highest point on the protrusion 200 residing in the same imaginary vertical plane (not shown) containing both the projection $M_{P1}$ and the sampling path $A_1-B$. As can be seen from FIGS. 8 and 9 for example, if the spacing line $A_1-B$ were elevated above point B while still remaining in the same imaginary vertical plane (not shown) containing both the projection $M_{P1}$ and the sampling path $A_1-Z_1$, then the spacing line $A_1-B$ no longer would be touching the surface of the smaller protrusion 200. In addition, if the spacing line $A_1-B$ were lowered beneath point B while still remaining in the same imaginary plane, then the spacing line $A_1-B$ would not be touching the highest point residing on the smaller protrusion 200 in the imaginary vertical plane including the projection $M_{P1}$ of the sampling path $A_1-Z_1$.

The first sampling path $A_1-Z_1$ shown in FIGS. 8 and 9 contains a second gap 250 between two adjacent protrusions. Accordingly, a second spacing measurement $S_2$ will be taken. One end point B of the straight line B-C defining the $S_2$ spacing measurement is identical to the end point B of the first straight line $A_1-B$ defining the first spacing measurement $S_1$. The opposite end point C of the straight line B-C defining the $S_2$ spacing measurement is once again where the surface of the adjacent protrusion 300 intersects the imaginary vertically extending plane containing both the projection $M_{P1}$ and the sampling path $A_1-Z_1$ followed by the profilometer.

Figure 10:
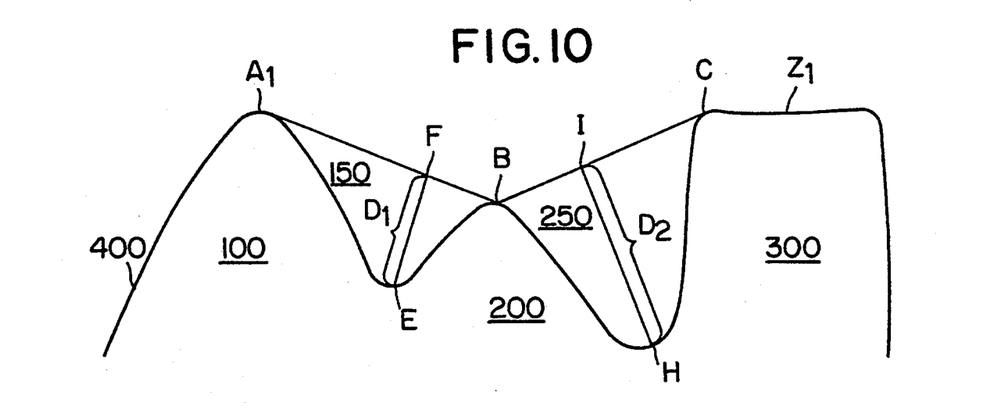

The second parameter to be measured from the graphical representation of the path taken by the profilometer probe is the depth measurement D of each gap encountered by the profilometer sampling probe as it follows the sampling path characterized by the projection $M_P$. As shown in FIG. 10 for example, the depth $D_1$ is defined by a line having one end point E at the bottom of the gap 150 and the opposite end point F at the perpendicular intersection with the straight line $A_1-B$ that defines the corresponding spacing distance $S_1$ that bridges gap 150. Similarly, since there is a second gap 250 in this sampling path $A_1-Z_1$, a second depth measurement $D_2$ is obtained in a similar fashion. One end point H of the $D_2$ depth measurement is the bottom of the second gap 250, and the opposite end point I is the normal intersection of the associated spacing line B-C which measures spacing distance $S_2$ that bridges second gap 250. Thus, there are two depth measurements $D_1$ and $D_2$ along this particular sampling path $A_1-Z_1$ with its projection measuring $M_{P1}$.

Figure 11:
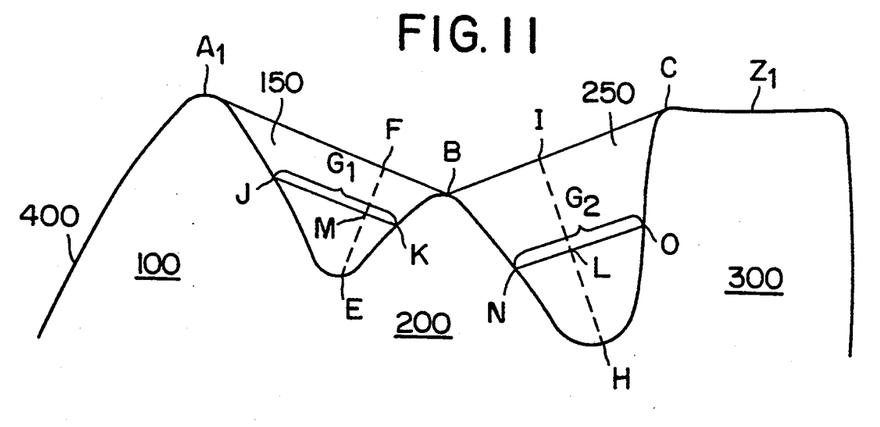

The third parameter is the gap width G of each gap. As shown in FIG. 11 for example, the gap width measurement $G_1$ is obtained by locating the two end points of the straight line which defines the gap width $G_1$ measurement. This line defining the gap width distance $G_1$ is parallel to the spacing line A-B defining the spacing measurement $S_1$ and resides in the same plane as the spacing line $A_1-B$ and as the projection $M_{P1}$ of the sampling path $A_1-Z_1$. The gap width measuring line is therefore also oriented so as to be perpendicular to the depth measuring line E-F (shown dashed in FIG. 11) defining the gap depth measurement $D_1$. The gap width measuring line intersects the depth measuring line E-F at the midpoint M of the line E-F which defines the gap depth measurement $D_1$. This is why the gap width measurement is sometimes referred to as the "gap half-height width measurement." The end points J and K of the gap width measuring line J-K are determined by the intersection of the gap width measuring line J-K with the opposed surfaces of the side walls of the adjacent protrusions 100, 200 which define the first gap 150. The length of the gap width line J-K equals the gap width measurement $G_1$.

As shown in FIG. 11, there is a second gap 250 encountered by the detecting probe of the profilometer as the profilometer travels to define the sampling path $A_1-Z_1$. The gap width measurement $G_2$ of the second gap 250 is obtained in the same fashion as the gap width measurement $G_1$ of the first gap 150. The second gap width line is oriented by perpendicularly intersecting the midpoint L of the second gap depth line H-I. The end points N and O of the second gap width measuring line N-O are determined by the intersection of the gap width measuring line N-O with the opposed surfaces of the side walls of the adjacent protrusions 200, 300 which define the second gap 250. The length of the second gap width line N-O equals the gap width measurement $G_2$.

Figure 12:
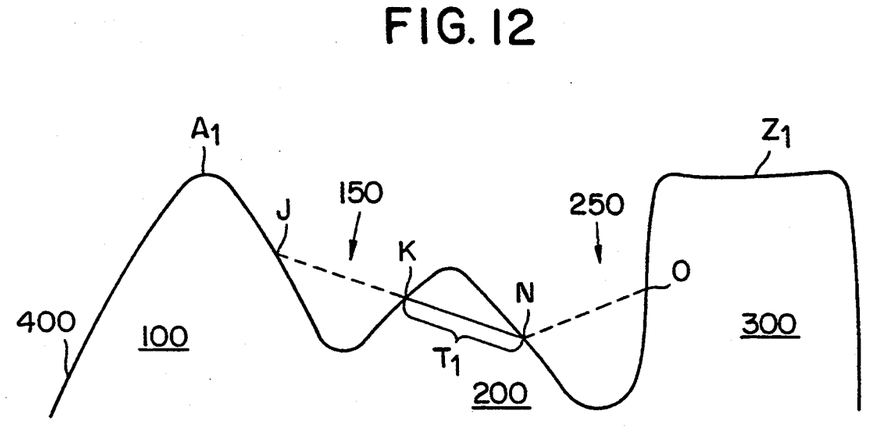

The fourth and final parameter is the thickness T of each protrusion that is wholly encompassed within the sampling path of the detecting probe of the profilometer. Only one such protrusion satisfies this definition in the sampling path $A_1-Z_1$ shown in FIGS. 8 and 12. As shown in FIG. 12 for example, the protrusion thickness measurement $T_1$ is obtained by measuring the length of the straight line K-N, which extends between the point K where the first gap width line J-K intersects the surface of the protrusion 200 on one end of line K-N and the point N where the second gap width line N-O defining the second gap width measurement $G_2$ of the second gap 250 intersects the surface of the protrusion 200 on the other end of protrusion thickness line K-N. Since K and N are both endpoints of their respective half gap width lines K-J and N-O, the thickness measurement T is sometimes referred to as the half-height thickness measurement.

Figure 7:
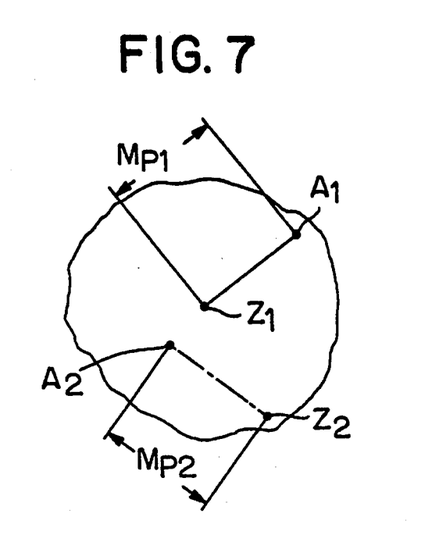
FIG. 7 schematically illustrates one method of choosing profilometer sampling paths that meet the sampling criteria for determining the roughness portion's attachment configuration according to the present invention.

In order to obtain the mean values of each of the four parameters, an additional 29 sample paths ($A_2-A_2$, $A_3-Z_3$, $A_4-Z_4$, * * * and $A_{30}-Z_{30}$) must be traced by the profilometer to yield a total of 30 profilometer sampling paths. More than 30 sampling paths can be used, but at least 30 profilometer sampling paths should be used in order to assure statistical accuracy. Each of the corresponding additional profilometer projections ($M_{P2}$, $M_{P3}$, $M_{P4}$, * * * and $M_{P30}$) must measure at least one-tenth of a millimeter. The additional profilometer projections ($M_{P2}$, $M_{P3}$, $M_{P4}$, * * * and $M_{P30}$) beyond the first profilometer projection $M_{P1}$ can be generated in a methodical fashion. To generate the additional 29 sample paths for taking the measures of the required parameters S, D, G, and T, one need only select another starting point $A_i$ and ending point $Z_i$ so that the line $A_i$-$Z_i$ has a projection $M_{Pi}$ therebetween, wherein the projection $M_{Pi}$ is neither coincident nor parallel to the projection of any other sampling path. As shown schematically in FIG. 7 for example, the projection $M_{P2}$ of sampling path $A_2$-$Z_2$ is neither coincident nor parallel to the projection $M_{P1}$ of sampling path $A_1$-$Z_1$ or to any other projection $M_{Pi}$ of any other sampling path $A_i$-$Z_i$.

Once all of the calculations of each of the four parameters S, D, G, and T, are obtained in the manner described above, the mean value of each parameter is obtained as follows. Each of the calculated values of a given parameter (either S or D or G or T) is added together to yield a sum which is divided by the number of such values which were measured during the 30 sampling path movements of the profilometer. For a hypothetical example in which the 30 sampling movements of the profilometer produces 56 protrusion spacing measurements S, then each of these 56 spacing measurements are added together to obtain a sum of the 56 spacing distances ($S_1+S_2+S_3+$ * * * $+S_{56}=SUM_{56}$). Then this sum of the values for all of the spacing measurements for the 30 sampling paths of the profilometer is divided by the number (56 or in general terms "n") of spacing measurements to yield the mean value of the spacing distance in the region of the band 34 in which the measurements were taken.

$$S_{mean} = \frac{1}{n} \sum_{i=1}^{i=n} S_i$$

Once each of the mean values for each of the parameters is calculated, then each of these mean values is examined to determine whether it falls within the ranges that are required for the attachment configuration according to the present invention. In particular, the so-called peak-to-peak spacings (S) between adjacent protrusions must have a mean value of 1 to 10 $\mu m$. The depth (D) of the gaps must have a mean value of at least 0.5 $\mu m$. The so-called half-height width (G) of the gaps must have a mean value of between 0.5 to 5 $\mu m$. The so-called half-height thickness (T) of the protrusions must have a mean value of between 0.5 and 5 $\mu m$.

Figure 2:
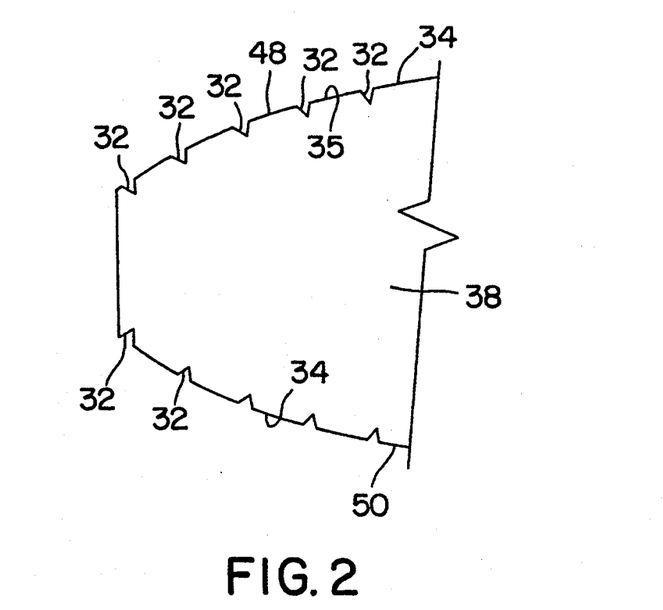
FIG. 2 is a detailed partial cross-sectional view taken of the embodiment shown in FIG. 1 and looking in the direction toward the letters A, A shown in FIG. 1 and a detailed view indicating the band 34 and its surface features.

As shown in FIGS. 1 and 2 for example, one embodiment of the attachment configuration includes circular grooves 32 disposed about the optical axis (not shown) with the mean value of the depths of said grooves in the range of from 1 to 4 micrometers, with the mean value of the half-thicknesses of the surface portion 35 between adjacent ones of grooves 32 measured in the radial direction in the range of from 1 to 4 micrometers, and with the mean value of the peak-to-peak spacings S across each groove measured a sampling path taken in the radial direction in the range of from 1 to 5 micrometers. Thus, the attachment configuration can have a more ordered structure so long as the basic parameters meet the specified mean values. The sizes of grooves 32 and intermediate surface portions 35 in FIG. 2 have been distorted larger than scale in order to facilitate illustration of this embodiment.

Figure 13:
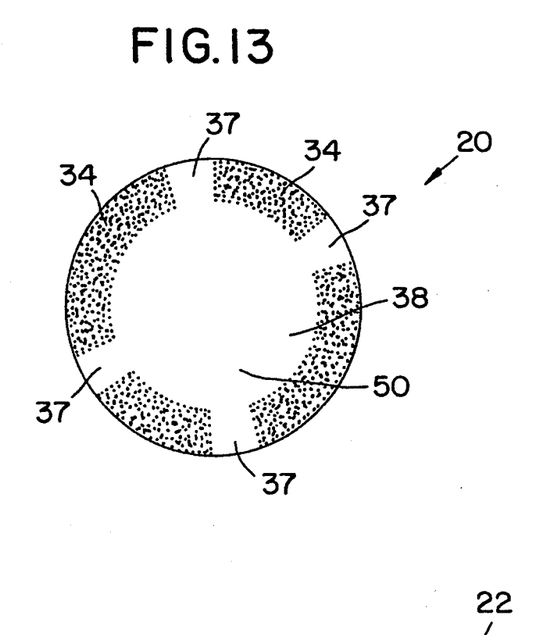
FIGS. 13, 14 and 15 are top plan views of alternative embodiments of the present invention.

As shown in FIGS. 4, 5 and 6 for example, two alternative preferred embodiments according to the present invention can also include a lens with an optic body diameter smaller than the original, natural lens of the patient, but with a haptic portion in the form of an outside disc-shaped portion 36 surrounding the optic body 38. The outside rim 40 of haptic portion 36 desirably carries the above mentioned band 34 of roughness 30 with the attachment configuration according to the present invention. In addition, as shown in FIGS. 4 and 5 for example, between the ring-shaped portion 36 carrying the band 34 and the optic body 38 at the center of the lens 22 of the present invention, the haptic portion 36 can be perforated with openings 42 for further weight reduction. Furthermore, as shown in FIGS. 4 and 13 for example, roughness portion 34 can be formed in the shape of a band having at least one sector 37 (indicated by the absence of stippling), and desirably a plurality of sectors 37, of interruptions of the roughness portion with configurations other than attachment configurations.

FIG. 6 is a cross-sectional view similar to FIG. 5, in which, however, the line of symmetry (indicated by dashed line 71) of the outside, disk shaped portion 36 formed as a frustoconical member, has been tilted in relation to the central plane (indicated by dashed line 70) of the lens body 38. The disk-shaped ring 36 can be tilted relative to the plane of the optic body of the lens toward either the posterior surface or the anterior surface of the lens by up to 30 degrees. This provides for some distance between the posterior or anterior surface of the lens and the posterior or anterior part of the lens capsule. This distance can prevent a direct contact between the two surfaces and, thus, prevent the formation of an opacity of this part of the capsule due to relative micromotions.

The roughness band 34 with the attachment configuration of the present invention can be formed on the periphery of optic body 38, whether lens 20 includes a haptic portion 36 or omits haptic portion 36. Moreover, the roughness portion or section 34 can be formed over substantially the entire posterior surface 50 of the lens body 38 (FIG. 14), as well as the posterior surface of the haptic portion 36 (FIG. 15), if any. In addition, the roughness section can be confined to an area shaped other than as a band 34. Also, the roughness section can be provided only on the outer periphery of haptic portion 36 in embodiments of lens 20 having haptic portion 36. Alternatively, the roughness section can be provided both on the outer periphery of haptic portion 36 and on the outer peripheral rim of optic body 38 of lenses which include haptic portions 36, whether perforated with openings 42 or not.

In the prior conventional implant devices, the haptic portions are embedded into the edge of the natural lens capsule, which, in turn, is surrounded by the cilliary muscle. The cilliary muscle can distort the eye's lens capsule and result in the posterior surface of the eye's lens capsule touching the surface of the implanted lens. These touching movements cause micromotions that result in the inflammation of the eye's posterior lens capsule. This inflammation eventually results in opacification of the posterior capsule tissue. Applicants determined that if the implanted lens is fixed to the posterior surface of the eye's lens capsule, then there can be no relative movement between the eye's posterior lens capsule and the implanted lens.

Figure 14:
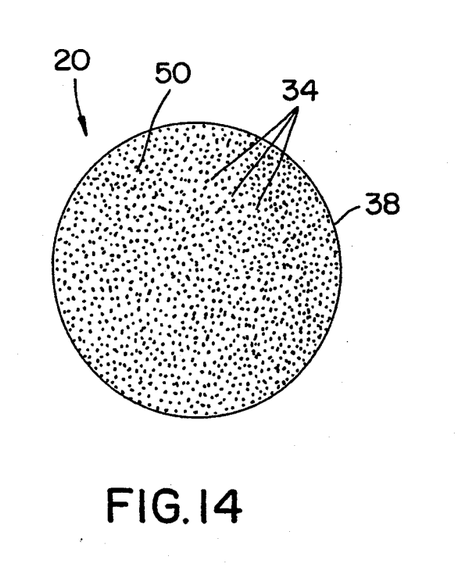
Figure 15:
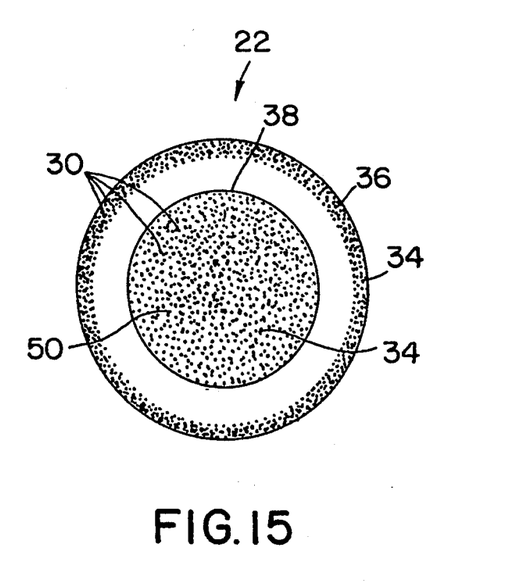

Therefore, as shown in FIGS. 14 and 15 for example, it is another embodiment of the present invention to extend the surface features from the band area 34 along the outside circumference of either the lens body 38 or the haptic, disk shaped ring portion 36, over the entire surface of the posterior side 50 of the lens. This embodiment has the further advantage of securely fastening the entire posterior eye capsule to the lens' posterior surface to prevent all relative micromotions which might remain possible even with a complete fixation along the outside circumference only. Any such micromovement has the potential to create an opacity of the posterior capsule. The surface features as defined in this invention by the attachment configuration parameters do not impair the optical properties of the lens in a way and to an amount that would compromise the visual ability of the recipient of such a lens.

The lens of the present invention desirably is formed of silicone or another biocompatible material which lends itself to the formation of the surface features required for promoting tissue acceptance and integration of such lens. For example, fluid forming polymers lend themselves to the formation of such surface features. Both the haptic portion 36 and optic body 38 desirably are formed as a unitary structure of the same material, but may be formed of an integrated structure of either the same or different materials. The latter is most likely when the shape of the lens makes it more convenient to form the surface features of the lens on the flatter surface of the outside rim portion 40 of the haptic portion 36 of the lens, rather than on the more curved outer periphery of the optic body 38.

The surface features of this invention can be realized in different ways depending on the material of the lens and the particular embodiment of the surface features. If the lens is manufactured by injection molding, the surface features can be integrated in the appropriate surface portions of the mold. If the lens is manufactured mechanically, the surface features can be realized by controlled mechanical cutting or etching operations. Many different patterns of the surface features according to this invention can be realized by computer-controlled laser treatments as noted in U.S. Pat. No. 5,011,494 for example.

Since the formation of the surface features by the appropriate surface texturing process does not change the bulk properties of the lens, the lenses of the present invention could be foldable as those according to the state of the art and, thus, also need a similarly small incision for implantation. On unfolding, none of the parts of the lens of the present invention can reach out of the eye capsule. Because of the possibility of choosing the exact diameter that matches the given patient situation, there will be no excess forces along the periphery of the eye's lens cavity. The surface features of the present invention will provide intimate integration of the lens into the circumferential eye tissue. This integration of the lens with the eye tissue will anchor the lens and provide a seal between the lens and the eye capsule without any appended mechanical fastening apparatus such as the fibers, clips, loops, and/or staves and sutures etc. of the prior art. In addition, the formation of granulation tissue can be avoided as the forces are exerted by the lens on the adjacent tissue and the attachment configuration of the roughness band 34 have been shown to provide for direct contact to normally proliferating tissue.

What is claimed is:

1. An intraocular lens comprising:
   a. an optic body, said optic body defining an optical axis, said optic body defining an anterior surface, said optic body defining a posterior surface disposed generally opposite to said anterior surface, said optic body defining a periphery connecting said anterior surface with said posterior surface;
   b. at least said posterior surface of said optic body defining a roughness portion disposed close to said periphery of said optic body; and
   c. said roughness portion further defining an attachment configuration, wherein said roughness portion covers substantially said entire posterior surface of said optic body.

2. A lens as in claim 1, further comprising:
   d. a roughness portion disposed on said anterior surface close to said periphery of said optic body, said anteriorly disposed roughness portion defining an attachment configuration.

3. A lens as in claim 1, further comprising:
   d. a haptic portion in the form of an annular disk-shaped ring extending from the periphery of and surrounding said optic body.

4. A lens according to claim 3, wherein said optic body defines a central plane disposed substantially symmetrically with respect to said anterior and posterior surfaces and perpendicular to said optic axis, said haptic portion defines an anterior surface and a posterior surface disposed opposite to said anterior surface, said haptic portion further defining a frustoconical member disposed generally symmetrically with respect to said anterior and posterior surfaces of said haptic portion, said frustoconical member of said haptic portion is tilted by up to 30 degrees with regard to said central plane of said optic body.

5. A lens as in claim 4, wherein said haptic portion defines at least one perforation.

6. A lens as in claim 3, wherein at least one perforation is defined through said haptic portion.

7. A lens as in claim 1, wherein said attachment configuration includes a plurality of gaps and protrusions forming said posterior surface.

8. A lens as in claim 7, wherein the mean value of the widths of said gaps is from 1 to 4 micrometers, the mean value of the thicknesses of said protrusions is from 1 to 4 micrometers, the mean value of the depths of the gaps is at least 0.5 micrometers, and the mean value of the spacings between the gaps is in the range from 1 to 4 micrometers.

9. A lens as in claim 1, wherein said attachment configuration includes circular grooves disposed about said optical axis.

10. A lens as in claim 9, wherein the mean value of the depths of said grooves falls in the range of from 1 to 4 micrometers, the mean value of the half-thicknesses of the surface portion between adjacent ones of said grooves measured in the radial direction falls in the range of from 1 to 4 micrometers, and the mean value of the peak-to-peak spacings between adjacent grooves measured in the radial direction falls in the range of from 1 to 5 micrometers.

11. An intraocular lens, comprising:
   a. an optic body, said optic body defining an optical axis, said optic body defining an anterior surface, and said optic body defining a posterior surface disposed generally opposite to said anterior surface;

b. a haptic portion in the form of an annular disk-shaped ring extending from and surrounding said optic body, said ring defining an anterior surface, said ring defining a posterior surface disposed generally opposite to said anterior surface, said ring defining a periphery connecting said anterior surface of said ring to said posterior surface of said ring, and at least said posterior surface of said ring defining a roughness portion disposed close to said periphery of said ring; and c. said roughness portion further defining an attachment configuration, wherein said roughness portion covers substantially said entire posterior surface of said optic body.

12. A lens as in claim 11 having a periphery wherein said haptic portion defines at least one perforation disposed between said roughness portion and said periphery of said intraocular lens.

13. A lens according to claim 11, wherein said optic body defines a central plane disposed substantially symmetrically with respect to said anterior and posterior surfaces of said optic body and perpendicular to said optic axis, said haptic portion defines an anterior surface and a posterior surface disposed opposite to said anterior surface, said haptic portion further defining a frustoconical member disposed generally symmetrically with respect to said anterior and posterior surfaces of said haptic portion, said frustoconical member of said haptic portion is tilted by up to 30 degrees with regard to said central plane of said optic body.

14. A lens as in claim 11, wherein said attachment configuration includes a plurality of gaps and protrusions forming said posterior surface.

15. A lens as in claim 14, wherein the mean value of the widths of said gaps is from 1 to 4 micrometers, the mean value of the thicknesses of said protrusions is from 1 to 4 micrometers, the mean value of the depths of the gaps is at least 0.5 micrometers, and the mean value of the spacings between the gaps is in the range from 1 to 4 micrometers.

* * * * *

UNITED STATES PATENT AND TRADEMARK OFFICE
CERTIFICATE OF CORRECTION

PATENT NO. : 5,405,385
DATED : April 11, 1995
INVENTOR(S) : Heimke et al

It is certified that error appears in the above-identified patent and that said Letters Patent is hereby corrected as shown below:

On the title page, item [75]:
Delete Frank M. Polack as an inventor.

Column 8, line 62: change the second occurrence of $A_2$ to --$Z_2$--.

Column 12, line 1: after the word "lens" insert --,--.

Column 13, line 15: after the word "periphery" insert --,--.

Signed and Sealed this

Twentieth Day of June, 1995

Attest:

BRUCE LEHMAN

Attesting Officer

Commissioner of Patents and Trademarks